US00PP31954P3

(12) United States Plant Patent
van Langen

(10) Patent No.: US PP31,954 P3
(45) Date of Patent: Jul. 7, 2020

(54) ***HAWORTHIA* HYBRID PLANT NAMED 'AMIHAW1811'**

(50) Latin Name: ***Haworthia limifolia* x *Gasteria* sp.**
Varietal Denomination: AMIHAW1811

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 16/501,724

(22) Filed: May 29, 2019

(65) Prior Publication Data

US 2019/0373792 P1 Dec. 5, 2019

(30) Foreign Application Priority Data

May 29, 2018 (QZ) ..... PBR 2018/1401

(51) Int. Cl.
*A01H 6/00* (2018.01)
*A01H 5/12* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Haworthia* hybrid plant named 'AMIHAW1811', which is characterized by spirally-arranged, dark green and glossy foliage with near-white orbicular protuberances arranged in irregular transverse rows across the upper and lower leaf surfaces and small near-white teeth along the length of the margins. The new variety has shown to be uniform and stable in the resulting generations from asexual propagation.

4 Drawing Sheets

Latin name of the genus and species: The Latin name of the genus and species of the novel variety disclosed herein is *Haworthia limifolia* x *Gasteria* sp.

Variety denomination: The inventive variety of *Haworthia* hybrid disclosed herein has been given the variety denomination 'AMIHAW1811'.

CROSS REFERENCE TO RELATED APPLICATIONS

This application claims priority to the Community Plant Variety Rights application number 2018/1401, filed May 29, 2018, which is herein incorporated by reference.

BACKGROUND OF THE INVENTION

Parentage: 'AMIHAW1811' is a seedling selection resulting from the controlled pollination of an unnamed *Haworthia limifolia* plant (not patented), the seed parent, with *Gasteria* hybrid 'Green Star' (U.S. Plant Pat. No. 24,763), the pollen parent. The crossing was made by the inventor in the winter of 2014 at a commercial greenhouse in Heerhugowaard, the Netherlands. In the summer of 2015, one seedling was observed which exhibited unique growth and foliage characteristics. After confirming the stability of the unique characteristics first observed, the new plant was selected for commercialization and given the name, 'AMIHAW1811'.

Asexual Reproduction: Asexual reproduction of the new cultivar 'AMIHAW1811', by way of rooting leaf cuttings, was first initiated in the summer of 2016 at the inventor's commercial greenhouse in Heerhugowaard, the Netherlands.

Through four subsequent generations, the unique features of this cultivar have proven to be stable and true to type.

SUMMARY OF THE INVENTION

The cultivar 'AMIHAW1811' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIHAW1811'. These characteristics in combination distinguish 'AMIHAW1811' as a new and distinct *Haworthia* hybrid cultivar:

1. 'AMIHAW1811' exhibits spirally-arranged succulent foliage in a basal rosette; and
2. 'AMIHAW1811' exhibits relatively small and thick foliage; and
3. 'AMIHAW1811' exhibits foliage with small, near-white teeth along the length of the margins and distal portion of the abaxial midrib; and
4. 'AMIHAW1811' exhibits dark green, moderately glossy foliage with near-white orbicular protuberances densely covering the abaxial and adaxial surfaces.

BOTANICAL DESCRIPTION OF THE PLANT

Figure 1:
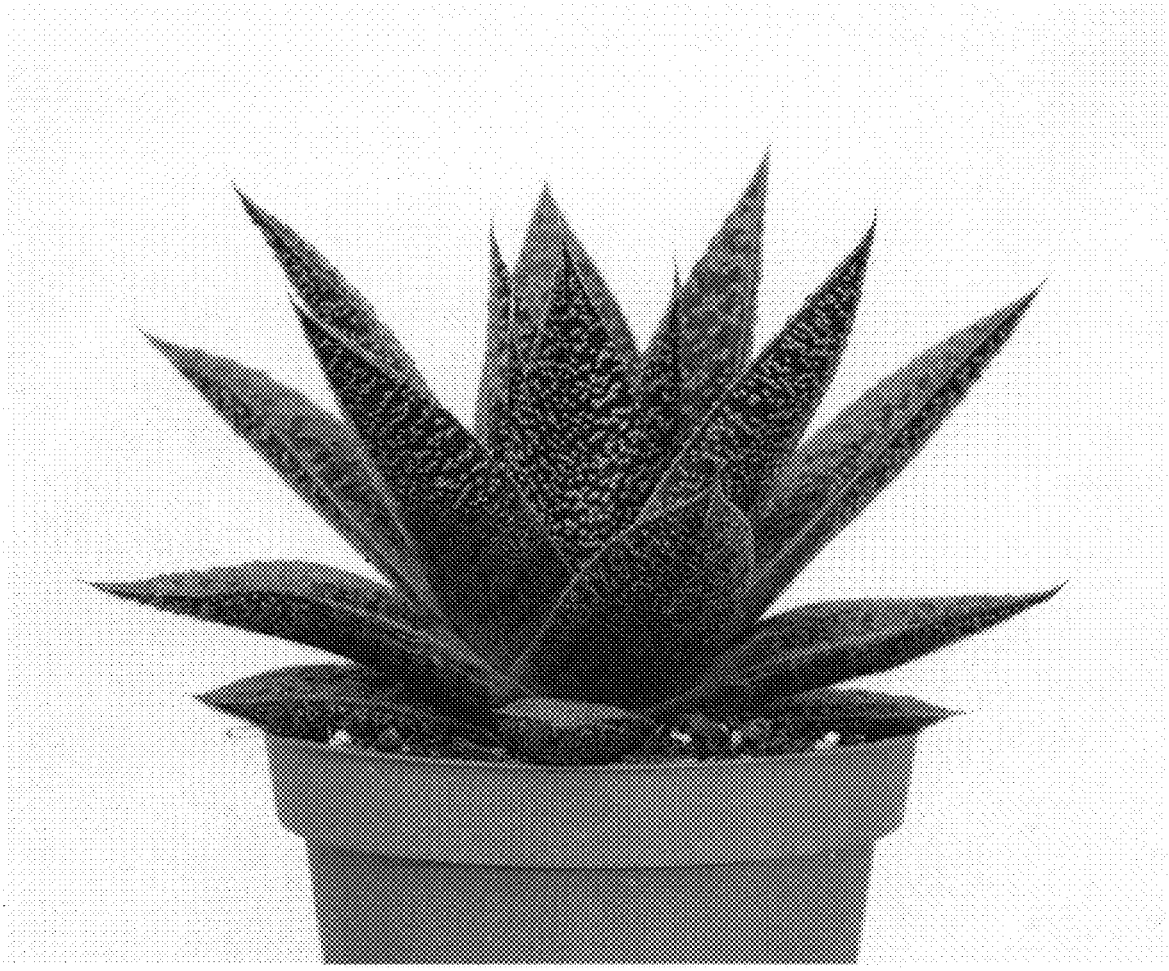
FIG. 1 illustrates, as nearly true as it is reasonably possible to make the same in color photographs of this type, an exemplary plant of 'AMIHAW1811' grown in a commercial greenhouse in Heerhugowaard, the Netherlands. This plant is approximately 1 year old, shown planted in a 11 cm container.
Figure 2:
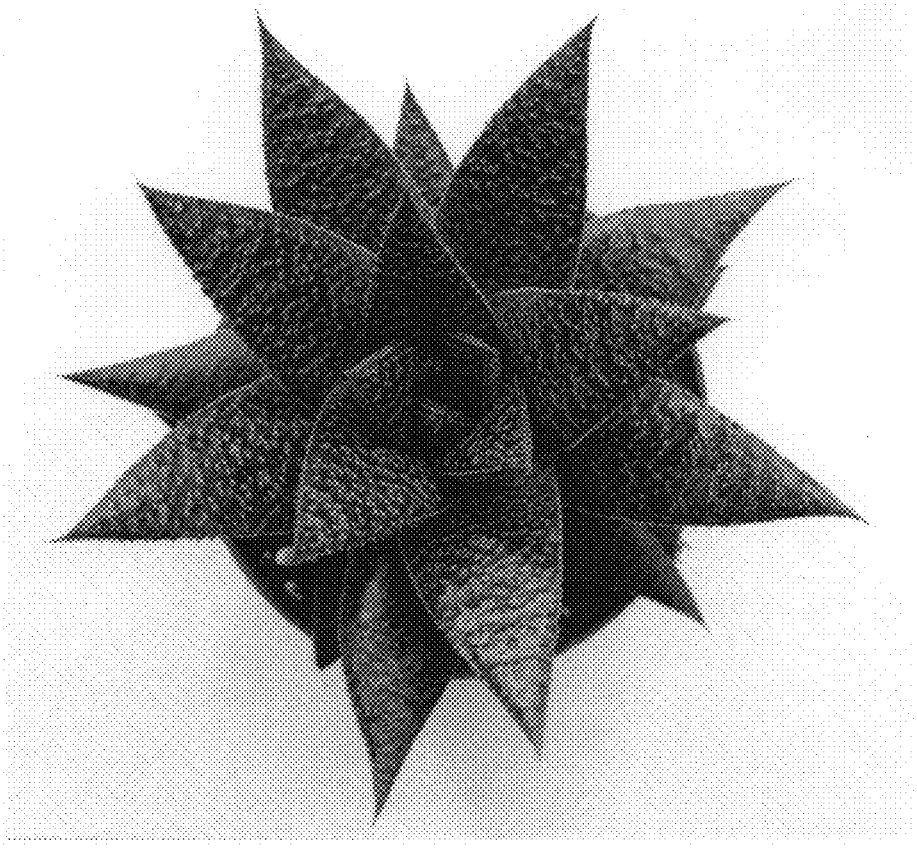
FIG. 2 illustrates, as nearly true as it is reasonably possible to make the same in color photographs of this type, the typical foliage arrangement of 'AMIHAW1811'.
Figure 3:
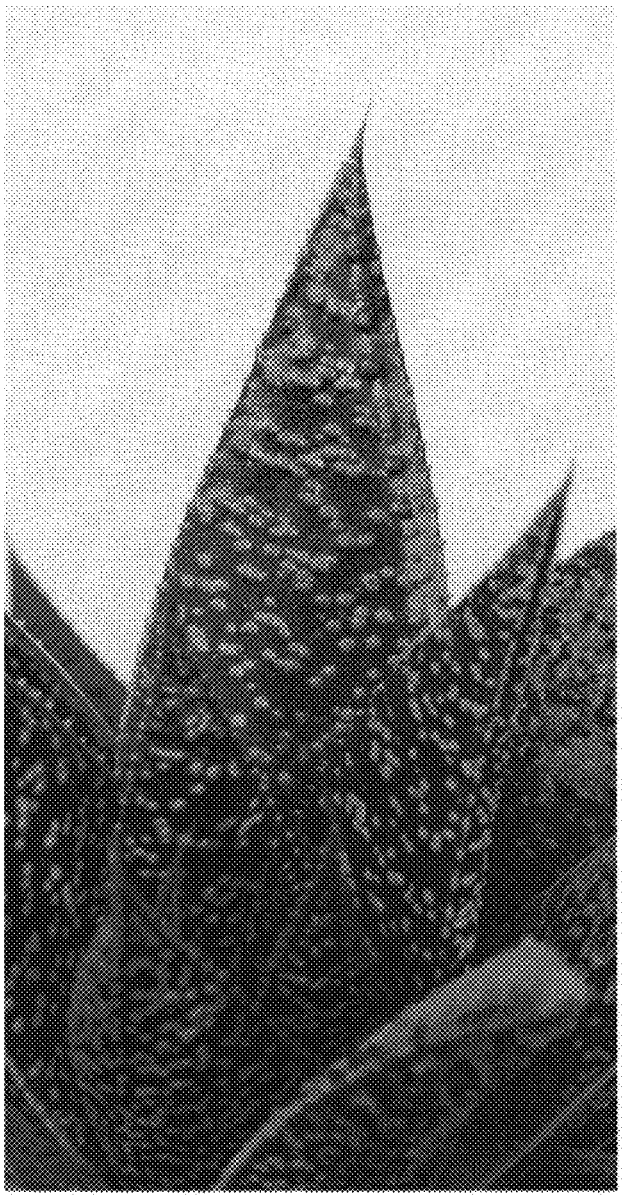
FIG. 3 illustrates, as nearly true as it is reasonably possible to make the same in color photographs of this type, the adaxial surface of the mature foliage 'AMIHAW1811'.
Figure 4:
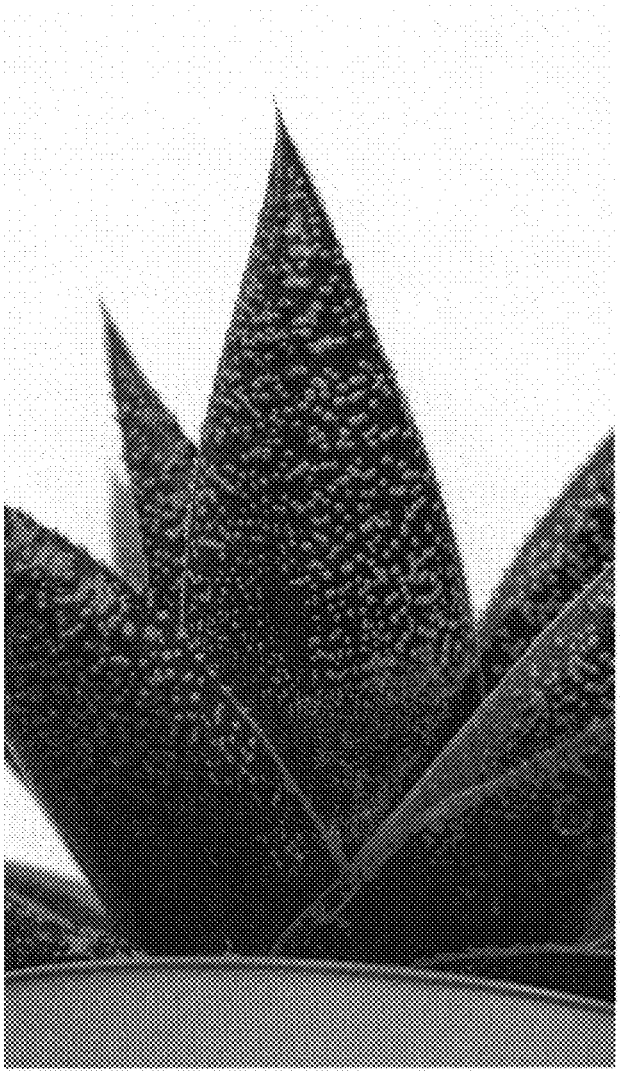
FIG. 4 illustrates, as nearly true as it is reasonably possible to make the same in color photographs of this type, the abaxial surface of the mature foliage 'AMIHAW1811'.

The following observations and measurements made in April of 2019 describe averages from a sample set of six specimens of 1 year-old 'AMIHAW1811' plants grown in 11 cm nursery containers at commercial greenhouse in Heerhugowaard, the Netherlands. Plants were produced using conventional greenhouse production protocols for *Haworthia* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIHAW1811' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIHAW1811' and a comparison with the parents and closest known comparator is provided below.

Plant description:

*Growth habit*.—Succulent perennial with foliage growing in a stemless, non-branched basal rosette.

*Plant shape*.—Flattened globular.

*Height from soil level to top of foliar plane*.—9.3 cm.

*Plant spread*.—Average of 15.9 cm.

*Growth rate*.—Slow to moderately fast.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in a 10.5 cm container.

*Disease and pest resistance or susceptibility*.—Neither resistance nor susceptibility to typical *Haworthia* or *Gasteria* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Spirally arranged in a rosette.

*Division*.—Simple.

*Attachment*.—Sessile.

*Quantity*.—24 leaves per rosette.

*Shape*.—Ovate, succulent foliage.

*Dimensions*.—9.2 cm long, 3.3 cm wide, and 1.1 cm thick, on average.

*Aspect*.—Slightly concaved and carinate.

*Attitude*.—Juvenile foliage at the center of the rosette is held upward to slightly outward; foliage becomes progressively more relaxed towards the outer whorls of mature foliage, at an average angle of 40 degrees from horizontal.

*Apex*.—Apiculate, with a soft mucronate tip.

*Base*.—Broad cuneate.

*Margin*.—Finely dentate; teeth have an average length of 0.1 cm and are colored green-white, nearest to RHS 157D. Margins are not undulated or lobed.

*Texture, adaxial surface*.—Glabrous and densely covered with orbicular protuberances; protuberances are approximately 0.1 cm high and 0.1 cm in diameter, at maturity.

*Texture, abaxial surface*.—Glabrous and densely covered with orbicular protuberances; protuberances are approximately 0.1 cm high and 0.1 cm in diameter, at maturity. The distal one-third portion of the midrib is finely dentate; teeth have an average length of 0.75 mm and are colored green-white, nearest to RHS 157A.

*Luster, adaxial surface*.—Moderately glossy.

*Luster, abaxial surface*.—Moderately glossy.

*Color*.—Juvenile foliage, adaxial surface — Nearest to in between green and yellow-green, RHS NN137A and 147A, and fading to yellow-green towards the base, nearest to RHS 148D; protuberances are colored yellow-green, nearest to RHS 145B. Juvenile foliage, abaxial surface — Green, nearest to RHS NN137A, and fading to yellow-green towards the base, nearest to RHS 148D; protuberances are colored yellow-green, nearest to RHS 147D. Dentate teeth on the midrib are green-white, nearest to RHS 157A. Mature foliage, adaxial surface — Nearest to in between yellow-green and greyed-green, RHS 147A and N189A; fading to greyed-white towards the base, nearest to a mixture of RHS 156B and 156C; protuberances are colored yellow-green, nearest to RHS 146C. Mature foliage, abaxial surface — Yellow-green, nearest to RHS 147A, and fading to a mixture of greyed-white and greyed-orange, RHS 156B and N170D; protuberances are colored yellow-green, nearest to RHS 146B. Dentate teeth on the midrib are green-white, nearest to RHS 157A.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIHAW1811' differ from the seed parent, an unnamed *Haworthia limifolia* (not patented), in the following characteristics described in Table 1 below.

TABLE 1

| Characteristic | 'AMIHAW1811' | Haworthia limifolia seed parent |
|---|---|---|
| Rate of growth. | Faster than the seed parent. | Slower than 'AMIHAW1811'. |
| Plant size. | Larger than the seed parent. | Smaller than 'AMIHAW1811'. |
| General coloration of the mature foliage. | Dark green. | Greyed-green. |
| Foliage length. | Longer than the seed parent. | Shorter than 'AMIHAW1811'. |
| Leaf protuberances. | Orbicular protuberances densely cover the leaf surface; protuberances are randomly placed. | Conspicuous transverse linear protuberances presenting as raised ribs across the leaf surface. |
| General coloration of leaf protuberances. | Lighter green when compared to the rest of the leaf surface. | Nearly the same color green as the leaf surface. |

Plants of the new cultivar 'AMIHAW1811' differ from the pollen parent, *Gasteria* hybrid 'Green Star' (U.S. Plant Pat. No. 24,763), in the following characteristics described in Table 2 below.

TABLE 2

| Characteristic | 'AMIHAW1811' | 'Green Star' |
|---|---|---|
| Foliage attitude. | More upright than 'Green Star'. | More relaxed than 'AMIHAW1811'. |
| Foliage thickness. | Thicker than 'Green Star'. | Thinner than 'AMIHAW1811'. |

TABLE 2-continued

| Characteristic | 'AMIHAW1811' | 'Green Star' |
|---|---|---|
| General coloration of the mature foliage. | Darker shade of green than 'Green Star'. | Lighter shade of green than 'AMIHAW1811'. |

COMPARISONS WITH THE CLOSEST KNOWN COMPARATOR

Plants of the new cultivar 'AMIHAW1811' differ from the closest known commercial comparator, the common form of the species *Gasteria* sp. 'Flow' (not patented), in the following characteristics described in Table 3 below.

TABLE 3

| Characteristic | 'AMIHAW1811' | 'Flow' |
|---|---|---|
| General coloration of the mature foliage. | Darker shade of green than 'Flow'. | Lighter shade of green than 'AMIHAW1811'. |
| Foliage length. | Longer than 'Flow'. | Shorter than 'AMIHAW18111'. |
| Foliage thickness. | Thicker than 'Flow'. | Thinner than 'AMIHAW1811'. |
| Prominence of leaf protuberances. | More prominent. | Less prominent. |

That which is claimed is:

1. A new and distinct variety of *Haworthia* hybrid plant named 'AMIHAW1811', substantially as described and illustrated herein.

* * * * *